(12) United States Patent
Entrekin et al.

(10) Patent No.: US 6,530,885 B1
(45) Date of Patent: Mar. 11, 2003

(54) SPATIALLY COMPOUNDED THREE DIMENSIONAL ULTRASONIC IMAGES

(75) Inventors: Robert R. Entrekin, Kirkland, WA (US); James R. Jago, Seattle, WA (US)

(73) Assignee: ATL Ultrasound, Inc., Bothell, WA (US)

( * ) Notice: Subject to any disclaimer, the term of this patent is extended or adjusted under 35 U.S.C. 154(b) by 0 days.

(21) Appl. No.: 09/528,339

(22) Filed: Mar. 17, 2000

(51) Int. Cl.[7] .................................................. A61B 8/00
(52) U.S. Cl. ........................ 600/437; 600/443; 128/916
(58) Field of Search ................................ 600/437, 443, 600/444, 447, 448, 449; 128/916

(56) References Cited

U.S. PATENT DOCUMENTS

| | | | |
|---|---|---|---|
| 5,653,235 A | | 8/1997 | Teo |
| 5,779,641 A | * | 7/1998 | Hatfield et al. ............. 600/443 |
| 6,012,458 A | * | 1/2000 | Mo et al. .................... 600/437 |

OTHER PUBLICATIONS

Moskalik et al., "Registration of Three–Dimensional Compound Ultrasound Scans of the Breast for Refraction and Motion Correction," Ultrasound in Med. & Bio., vol. 21, No. 6, pp. 769–778, 1995, Elsevier Science Ltd.

Rohling et al., "Automatic Registration of 3–D Ultrasound Images," Ultrasound in Med. & Bio., vol. 24, No. 6, pp. 841–854, 1998, World Federation for Ultrasound in Medicine & Biology.

Rohling et al., "Three–Dimensional Spatial Compounding of Ultrasound Images," Medical Image Analysis (1996/7), vol. 1, No. 3, pp. 177–193, Oxford University Press.

* cited by examiner

*Primary Examiner*—Marvin M. Lateef
*Assistant Examiner*—Maulin Patel
(74) *Attorney, Agent, or Firm*—W. Brinton Yorks, Jr.

(57) ABSTRACT

An ultrasonic probe is moved to scan a volumetric region of the body. As it is moved, targets within the region are interrogated from multiple look directions. The echo data from the multiple look directions are compounded to form spatially compounded image data, which is processed for display in a three dimensional display format.

41 Claims, 7 Drawing Sheets

SPATIALLY COMPOUNDED THREE DIMENSIONAL ULTRASONIC IMAGES

This invention relates to ultrasonic diagnostic imaging and, in particular, to spatially compounded three dimensional ultrasonic imaging systems and methods.

Co-pending U.S. patent applications Ser. No. 09/335,058 and 09/435,118 describe apparatus and methods for performing real time spatial compounding of ultrasonic diagnostic images. Spatial compounding is an imaging technique in which ultrasound image data of a given target that has been obtained from multiple vantage points or look directions are combined into a single compounded image by combining the data for example by linearly or nonlinearly averaging or filtering. The compounded image typically shows lower speckle and better specular reflector delineation than conventional ultrasound images produced from a single look direction.

A number of techniques have been proposed in the literature for extending the application of spatial compounding to three dimensional (3D) volumetric ultrasound image data. Three dimensional image data can benefit from spatial compounding, as the speckle reduction and better reflector delineation can improve the ability to better render a three dimensional image, since clutter effects can debilitate the 3D rendering process. At one end of the 3D spatial compounding spectrum is the acquisition of the image data by a large, static two dimensional ultrasonic transducer array as described for example in U.S. Pat. No. 5,653,235. As mentioned in this patent, if the two dimensional array can electronically steer ultrasound beams widely over a volumetric region, spatially compounded 3D images can be acquired without the need for the operator to move the probe physically. However, such a fully electronically controlled and physically motionless system requires tremendous technological sophistication and is not yet commercially feasible. At the other end of the spectrum are the systems and techniques described by Moskalik et al. and Rohling et al. in "Registration of Three-dimensional Compound Ultrasound Scans of the Breast for Refraction and Motion Correction, A. Moskalik et al., Ultrasound in Med. & Biol., vol. 21 no. 6, pp 769–78 (1995) and "Automatic Registration of 3-D Ultrasound Images, R. Rohling et al., Ultrasound in Med. & Biol., vol. 24 no. 6, pp 841–54 (1998). These techniques involve much less sophisticated systems and operate by acquiring sequential planes of ultrasonic images as the operator moves a 1D transducer array across the patient's body. In second and subsequent scans the orientation of the transducer probe with respect to the body is changed by tipping or tilting the probe differently each time. Each scan thereby acquires a sequence of ultrasound images at a different orientation. The images from the different scans are then combined after being registered, usually by the use of a position sensor attached to the transducer probe. While requiring far less complex equipment as compared to the fully electronically steered approach, the performance of multiple scans to acquire image data for compounding makes the technique susceptible to motional effects and registration inaccuracies. Such problems can introduce blurring into the image data, which can adversely affect the 3D image rendering process. It would be desirable to take an intermediate approach which does not have the complexity and attendant cost of the fully electronically steered approach but avoids the inaccuracies introduced by the multiple scan approaches.

In accordance with the principles of the present invention apparatus and techniques are provided for producing spatially compounded three dimensional ultrasonic images. Scanning is performed by moving a probe to scan a three dimensional volume of the body. As the probe is moved, multiple scans are performed electronically in different look directions. At the end of a single scan image data is provided from multiple look directions of a target so that a spatially compounded three dimensional image can be formed. By acquiring the multiple look directions in a single scan, motional effects and the need for intensive registration processing are significantly reduced. Multiple scans can be performed and compounded, which increase the speckle reduction as a function of the product of the number of scans and look directions.

Figure 1:
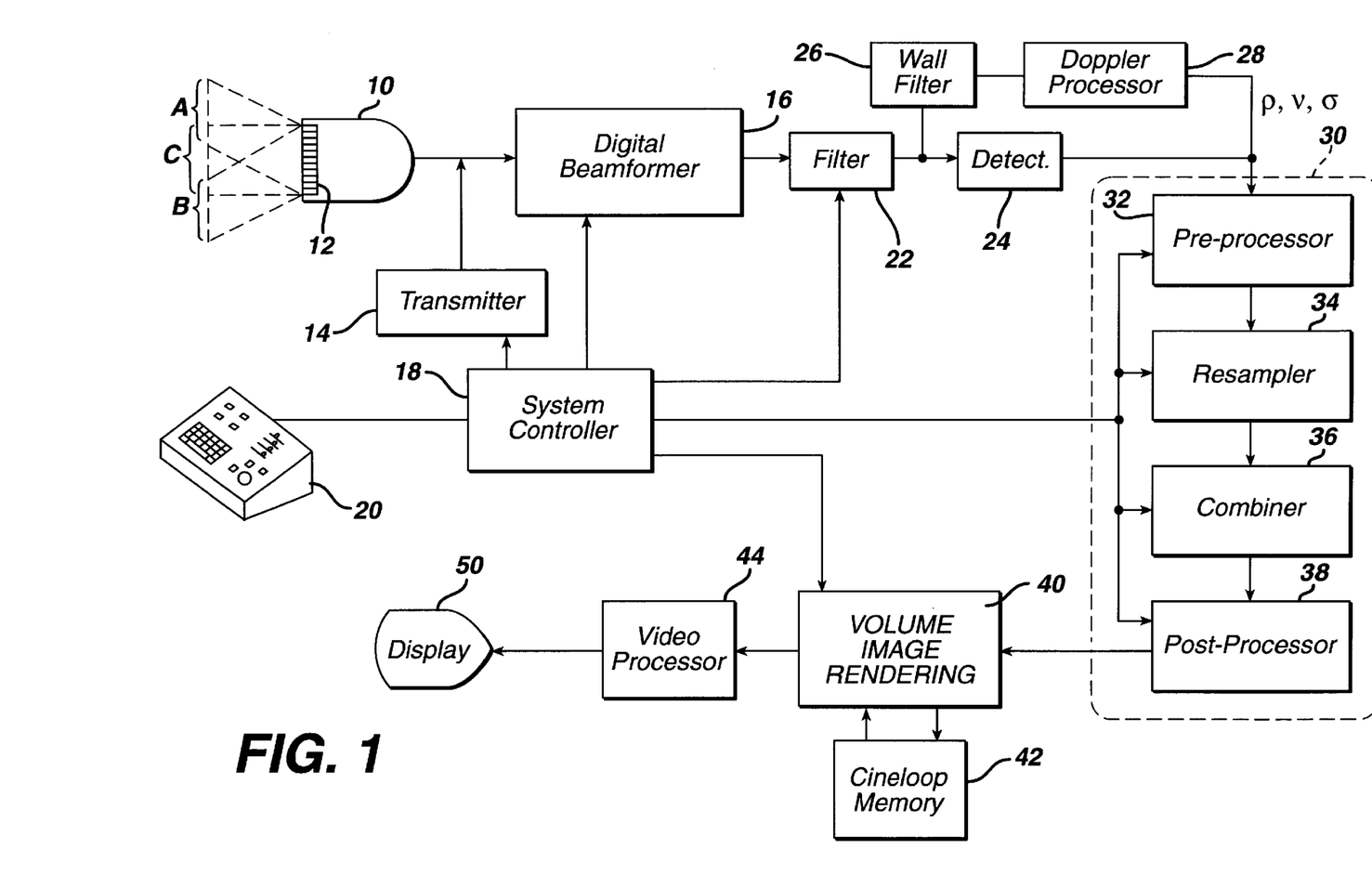
FIG. 1 illustrates in block diagram form an ultrasonic diagnostic imaging system constructed in accordance with the principles of the present invention.

Referring first to FIG. 1, an ultrasonic diagnostic imaging system is shown in block diagram form which performs ultrasonic spatial compounding of volumetric image information in accordance with the principles of the present invention. A scanhead 10 including an array transducer 12 transmits beams at different angles over an image field as denoted by the dashed rectangle C and parallelograms A and B. Three groups of scanlines are indicated in the drawing and denoted by A, B, and C with the scanlines of each group being steered at a different angle relative to the scanhead, illustrating the example of compounding three component image frames outlined by A, B, and C. The transmission of the beams is controlled by a transmitter 14 which controls the phasing and time of actuation of each of the elements of the array transducer so as to transmit each beam from a predetermined origin along the array and at a predetermined angle or steering direction, and focus. The echoes returned from along each scanline are received by the elements of the array, digitized as by analog to digital conversion (not shown), and coupled to a digital beamformer 16. The digital beamformer delays and sums the echoes from the array elements to form a sequence of focused, coherent digital echo samples along each scanline. The transmitter 14 and beamformer 16 are operated under control of a system controller 18, which in turn is responsive to the settings of controls of a user interface 20 operated by the user of the ultrasound system. The system controller controls the transmitter to transmit the desired number of scanline groups at the desired angles, focuses, transmit energies and frequencies. The system controller also controls the digital beamformer to properly delay and combine the received echo signals for the apertures and image depths used.

The scanline echo signals are filtered by a programmable digital filter 22, which defines the band of frequencies of interest. When imaging harmonic contrast agents or performing tissue harmonic imaging the passband of the filter 22 is set to pass harmonics of the transmit band. For fundamental frequency imaging the fundamental frequency band is passed, and the two bands may be separated and passed for blended harmonic and fundamental frequency imaging. Harmonic frequency separation may be performed by the technique known as pulse inversion and described in U.S. Pat. No. 5,706,819 and 5,951,478. The filtered signals are detected by a detector 24 for B mode imaging and/or coupled to a wall filter 26 for Doppler imaging. In a preferred embodiment the filter 22 and detector 24 include multiple filters and detectors so that the received signals may be separated into multiple passbands, individually detected and recombined to reduce image speckle by frequency compounding. For B mode imaging the detector 24 will perform amplitude detection of the echo signal envelope. For Doppler imaging the received signals first undergo wall filtering to pass desired Doppler signals and reject undesired signals, such as undesired signals from slow moving or stationary tissue when imaging bloodflow. When tissue motion is to be Doppler imaged, the wall filter may be set to reject only stationary tissue signals or the wall filter may be bypassed entirely with the system gain or sensitivity set to emphasize signals of greater amplitude. In a preferred embodiment wall filtering is performed by a mathematical matrix operation to reduce tissue motion effects when flow is being image or flow effects when moving tissue is being imaged. Ensembles of echoes are assembled for each point in the image and are Doppler processed by a Doppler processor 28 to produce estimates of the Doppler shift, Doppler power intensity p, velocity v or variance $\sigma$.

The Doppler and/or B mode signals are processed by spatial compounding in a processor 30. The signals applied to processor 30 are initially pre-processed by a preprocessor 32. The pre-processor 32 can preweight the signal samples if desired with a weighting factor. The samples can be preweighted with a weighting factor that is a function of the number of component frames used to form a particular compound image. The pre-processor can also weight edge lines that are at the edge of one overlapping image so as to smooth the transitions where the number of samples or images which are compounded changes. The pre-processed signal samples may then undergo a resampling process in a resampler 34. Because the signal samples of each component frame are acquired from different look (steering) directions, the samples of the component frames, when overlaid, will generally not be in exact spatial registration with each other. The resampler 34 can spatially realign the estimates of each component frame into registration with a common estimate sample spatial reference in which the component frames are compounded. The resampler can also realign and register estimates of each component frame which have been misaligned due to anatomy or scanhead motion during acquisition or variations in the speed of sound during passage through the anatomy as described in U.S. patent application Ser. No. [09/335,059, filed Jun. 17, 1999]. The resampler can also effect scan conversion by resampling the data into the coordinates of a desired display orientation.

After resampling the image frames are compounded by a combiner 36. Combining may comprise summation, averaging, peak detection, temporal filtering, or other combinational means. The samples being combined may also be weighted prior to combining in this step of the process. Finally, post-processing is performed by a post-processor 38. The post-processor normalizes the combined values to a display range of values. Post-processing can be most easily implemented by look-up tables and can simultaneously perform compression and mapping of the range of compounded values to a range of values suitable for display of the compounded image. It may be desirable to employ spatially varying compression, with the range of compression varying as a function of the number of look directions being compounded at a particular point in the image.

The compounding process may be performed in estimate data space or in display pixel space. In a preferred embodiment spatial compounding is done with estimate space data, and the compounded image data is thereafter scan converted to display space data of the desired image format. The compound images may be stored in a Cineloop® memory 42 in either estimate or display pixel form. If stored in estimate form the images may be scan converted when replayed from the Cineloop memory for display. Following scan conversion B mode and Doppler images which are temporally proximal and of substantially the same image field may be overlaid to form an image of both compounded B mode image information and compounded Doppler image information. A Doppler image may also be combined with a non spatially compounded B mode image, which can result in a greater frame rate of display. The spatially compounded images, Doppler, B mode, or combined, are processed for display by a video processor 44 and displayed on an image display 50.

In accordance with the principles of the present invention, the spatially compounded image data is presented in a three dimensional display format by a volume image rendering processor 40. As will be explained in greater detail below, image data from a volumetric region which has undergone spatial compounding, either B mode or Doppler data, is processed by volume image rendering into a 3D display presentation. The rendering is controlled by rendering control signals selected by the user interface 20 and applied to the processor 40 by the system controller 18. The rendering control signals can precondition the processor 40 to render Doppler or tissue signal information, for instance, and/or to render the image data with opacity weighting which will enable flow to be viewed through a volume of tissue, for example. The Cineloop memory can be operated in support of the volume rendering processor by storing a sequence of dynamic parallax rendered images which are then replayed either directly to the video processor 44 or through the volume rendering processor first for scan conversion when un-scan converted images are stored in memory.

Since ultrasound signals acquired from different look directions will exhibit different speckle patterns, the combining of signals from different look directions will reduce image speckle artifacts. The different look directions will also provide better delineation of interfaces and boundaries, since no boundary or interface in the image will be viewed from only a tangential direction. Furthermore, Doppler and colorflow imaging are known to have an angle dependence between the ultrasound beam and the velocity of flow. As the angle increases, that is, the direction of blood flow or tissue motion is more perpendicular to the beam, the Doppler shift decreases. When it is fully perpendicular the mean Doppler shift frequency is zero. In an embodiment of the present invention in which flow or motion is viewed from different look directions, this zero dropout of the Doppler signal is prevented since flow or motion is always viewed from more than one angle.

Figure 2:
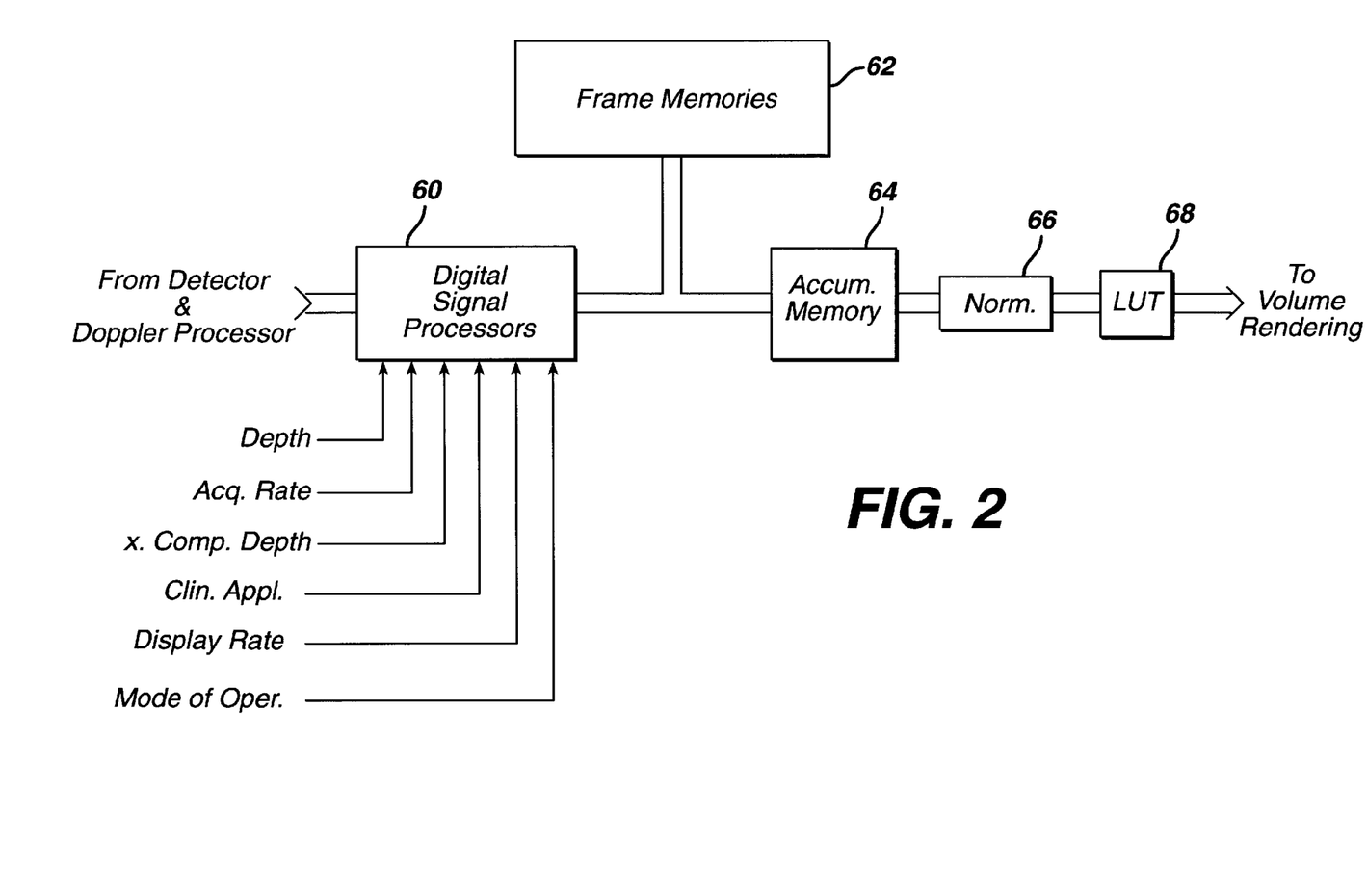
FIG. 2 illustrates in block diagram form a preferred implementation of the spatial compounding processor of FIG. 1.

FIG. 2 illustrates a preferred implementation of the spatial compounding processor 30 of FIG. 1. The processor 30 is preferably implemented by one or more digital signal processors 60 which process the image data in various ways. The digital signal processors 60 can weight the received image data and can resample the image data to spatially align pixels from look direction to look direction or frame to frame, for instance. The digital signal processors 60 direct the processed image frames to a plurality of frame memories 62 which buffer the individual image frames. The number of image frames capable of being stored by the frame memories 62 is preferably at least equal to the maximum number of image frames to be compounded such as sixteen frames. In a preferred embodiment the digital signal processors are responsive to control parameters including image display depth, depth of region of greatest compounding, clinical application, compound display rate, mode of operation, and acquisition rate for determining the number of images to compound at a given instant in time. The digital signal processors select component frames stored in the frame memories 62 for assembly as a compound image in accumulator memory 64. The compounded image formed in the accumulator memory 64 is weighted or mapped by a normalization circuit 66, then compressed to the desired number of display bits and, if desired, remapped by a lookup table (LUT) 68. The fully processed compounded image is then transmitted to the volume image rendering processor for rendering in a three dimensional display format.

Figure 3:
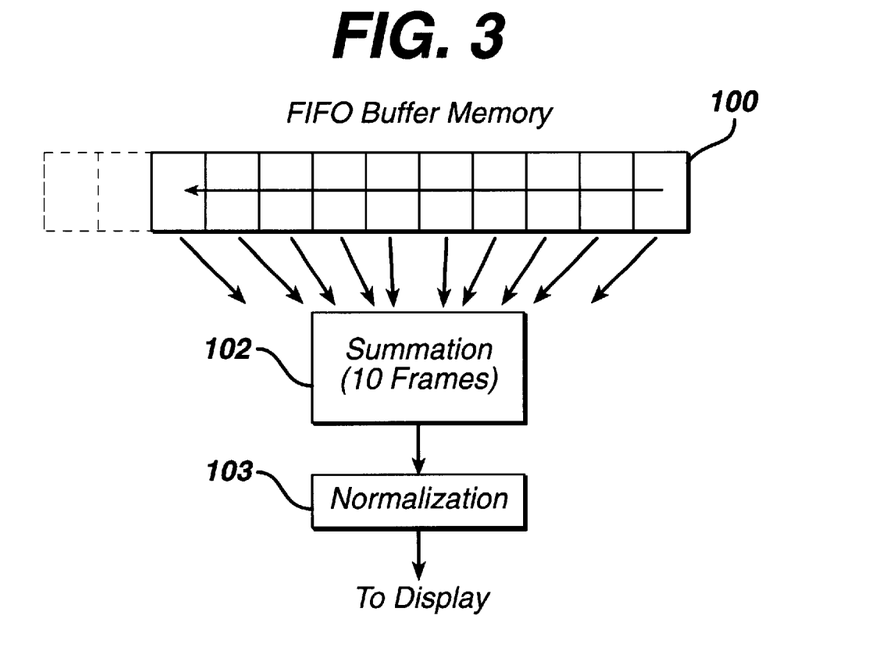
FIG. 3 illustrates in block diagram form a spatial compounding processor with frame memories and compound image accumulator.

One approach to implementing spatial compounding is to use a large FIFO memory buffer 100 to temporarily store the component image frames that will be compounded (typically by averaging, i.e., summing 102 and normalization 103) to form the final compounded image, as shown in FIG. 3. For example, if the acquired images are 512 pixels×512 pixels×1 byte and there are 10 images to be compounded, the buffer memory 100 would need to have a capacity of 2.5 megabytes. For real-time spatial compounding, where the compounded frames are generated either at the acquisition frame rate or at the display frame rate, the hardware that is performing the compounding must have sufficient bandwidth to access all of the frames in this buffer memory at the compounded frame rate, as well as have sufficient processing power to sum all of the frames and normalize the compounded frame at this rate. To proceed with the example above, if the required compounded frame rate is 60 Hz, the compound image processor would need a data bandwidth of at least 150 megabytes per second and would need to perform at least $150 \times 10^6$ multiply/accumulate operations per second.

Figure 4:
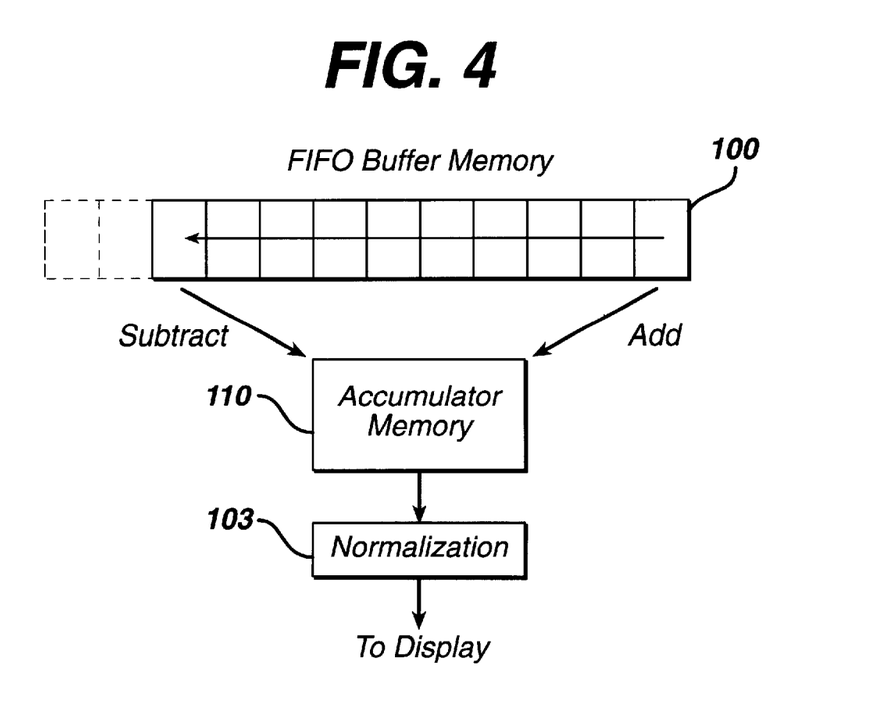
FIG. 4 illustrates in block diagram form a second spatial compounding processor using an accumulator which operates upon partially summed compound images.

Another compound image processor is shown in FIG. 4 which considerably reduces the bandwidth and processing requirements imposed on the processor. This embodiment is obtained by considering the summation involved in averaging to be a linear and associative (FIR) filtering operation. In FIG. 4 an accumulator memory 110, which preferably has sufficient bit depth to preserve the full precision of the compounded image, is initialized by summing the first N frames (where N is the number of component frames to be compounded). Subsequent compounded images are obtained by subtracting the oldest acquired frame (i.e., N−1 frames before the current frame, on the left of the FIFO in the drawing) from the summed framed in the accumulator memory 110 and adding the newest (most current) frame (on the right of the FIFO in the drawing) to the accumulator memory. The normalization 103 can be performed either on the input component frames before summation or on the summed image as it is read from the accumulator memory 110, prior to sending it on to other operations such as volume rendering.

In the example given above with 10 frames being compounded at a rate of 60 Hz, the data bandwidth required would be that needed to access the current frame and the oldest frame (i.e., N frames previous to the current frame) from the FIFO buffer memory 100, i.e., 30 megabytes per second, while the number of operations is that required to add and subtract these frames from the accumulator memory 110, i.e., approximately $30 \times 10^6$ multiply/accumulate operations per second. One of the advantages of this approach is that the bandwidth and processing requirements are independent of the number of component frames to be compounded—they depend only on the compounded frame rate. The extra memory required for the accumulator memory 110 would be 512×512×2 bytes, or 0.5 megabytes, which provides sufficient precision for up to 256 compounded frames.

One disadvantage of this approach is that the compounding operation is limited to operations that are linear and associative, such as addition and multiplication. Other operations, such as peak detection or median filtering, which do not follow linear combinatorial rules would not be possible with this embodiment. However, these operations would be possible with the compounding approach described in FIG. 3.

A further embodiment of the present invention, which further reduces the data bandwidth requirements, is possible if the output frame rate (i.e., the rate at which compounded images are generated) is substantially lower than the acquisition frame rate (i.e., the rate at which component images are acquired). This is a reasonable assumption when one considers that, if the compounded frames are generated at the acquisition rate, each compounded frame shares N−1 acquired frames in common with the previous compounded frame. In other words, there is typically a great deal of inherent persistence in real-time spatial compounding, the amount of persistence being directly proportional to the number of frames being compounded. Thus, to minimize the effects of motion induced blurring, it is desirable to maintain the highest possible acquisition rate. However, it may not be necessary to generate compounded images at the acquisition rate, bearing in mind the high temporal correlation between successive frames and the fact that the display rate may be lower than the acquisition rate.

Figure 5:
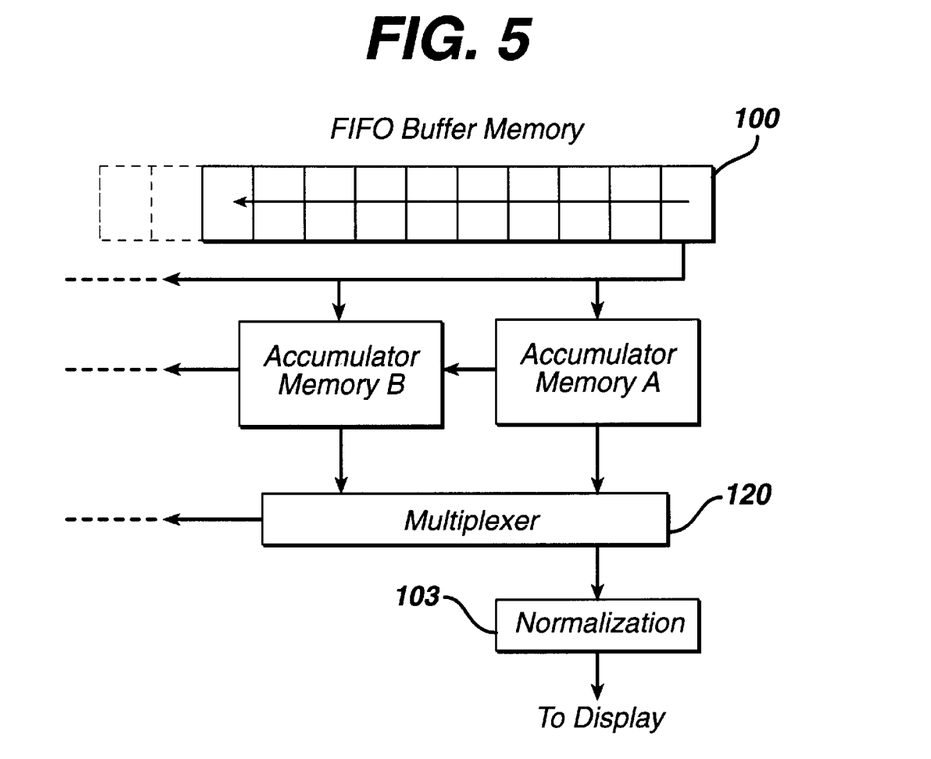
FIG. 5 illustrates in block diagram form another embodiment of the present invention which uses multiple accumulators to simultaneously process multiple compound images.

FIG. 5 shows another embodiment of the present invention using two (or more) accumulator memories A and B, where the output (display) frame rate is always a factor of CEIL(N/M) lower than the acquired frame rate, where N is again the number of component frames being compounded and M is the number of accumulators. The accumulator memories A and B are used to generate compounded images in a ping-pong fashion. For the case of two accumulators, memory A is initialized first by summing the first N frames, while memory B does not start accumulating until the (CEIL(N/2)+1) frame has been reached. Subsequently, each accumulator memory makes its compounded image available to a multiplexer 120 as soon as N consecutive frames have been summed. The accumulator memory is then immediately cleared before beginning a new accumulation of component frames. Since the accumulator memories are cleared for the averaging method of compounding, there is no need in this method to subtract the oldest acquired frames from the accumulated sum of frames in the memory—it is only necessary to add the newest frame to both accumulators. Furthermore, it is not necessary to have separate buffer memories for storage of the component frames, as there is no need to save component frames for subsequent subtraction. Thus, this embodiment can reduce the image buffer requirements of the ultrasound system. The multiplexer chooses the most recently accumulated compound image to be sent on for normalization 103 and display.

Using the previous example, an acquisition rate of 60 Hz with 10 compounded frames gives, with two accumulators, an output rate of 60/CEIL(10/2)=12 Hz. The data bandwidth needed to the FIFO is now only 15 megabytes per second, while the two accumulator memories require 1 megabyte of memory and $30 \times 10^6$ operations per second, the same as the previous embodiment. Although the output of both accumulator memories must be normalized, this can now be done at the output rate of 12 Hz for a total of approximately $6 \times 10^6$ operations per second, thus representing overall a 500% reduction in normalization processing requirements compared to the first embodiment. Another advantage of this method is that the compounding operator need no longer be associative (it still needs to be linear), so that operations such as peak detection are now possible.

Like the previous embodiment, the memory and processing requirements of this further embodiment are independent of the number of frames being compounded. However, higher output rates can be achieved by adding accumulators as indicated in FIG. 5 by the dashed lines, with a concurrent increase in processing requirements.

Yet another alternative for compounding component images is to employ a recursive IIR filter architecture. The recursive feedback of some fraction of the compounded data provides a controllable persistence in the compound image. The IIR filter can be constructed as an image accumulator having two sources of input data, one being new component image data and the other being a weighted portion of the compounded image data produced by the accumulator.

Figure 6:
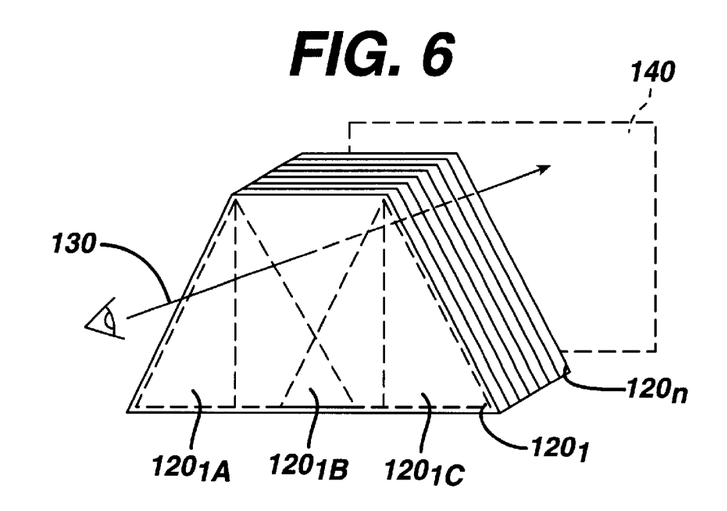
FIG. 6 illustrates a three dimensional rendering technique suitable for use in an embodiment of the present invention.

The volume image rendering processor 40 can operate to develop a 3D presentation of the spatially compounded volumetric image data in a variety of ways. The processor can delineate a surface on or within the volume and present a surface rendering of tissue or vasculature. The volume of data can be presented as a series of slices or a volumetric block of image data. Images can be formed of arbitrary planes passing through the volumetric image data to produce synthesized slice images, a three dimensional technique known as multi-planar reformatting. One preferred way to present the volumetric data is in a rendered form known as kinetic parallax. FIG. 6 illustrates a series of image slices $120_1$–$120_n$, which have been acquired from a volumetric region of the body. In this example each image is a compound image of three component images. The component frames $120_{1A}$, $120_{1B}$, and $120_{1C}$ are shown for the compound image $120_1$, which is nearest the viewer. The volumetric image data is projected onto a plane 140 by a number of projection lines, one of which is shown as projection line 130. A pixel for the projection plane 140 is produced by accumulating the image data along the projection line 130 in a predetermined manner. The image data along the projection line can be accumulated by summation, by integration, or by detecting the maximum, mean or average intensity along the projection line, for example. This process is repeated for a plurality of parallel and spatially distinct projection lines 130 until pixels are determined for the entire projection plane. The projection plane thus represents the volumetric data as seen from the particular projection line direction used. The process is repeated to produce a series of projection planes, each at a unique projection line direction. When the projection planes are displayed in rapid sequence in the order of progressively increasing or decreasing projection line directions, the volumetric region appears to rotate in three dimensions before the viewer. By adjusting the rendering parameters supplied by the system controller, the viewer has the option to render tissue or vasculature more or less intense or more or less opaque, for instance, enabling the viewer to see inside or through the volume and examine surfaces or structure or flow inside the volumetric region.

Figure 7:
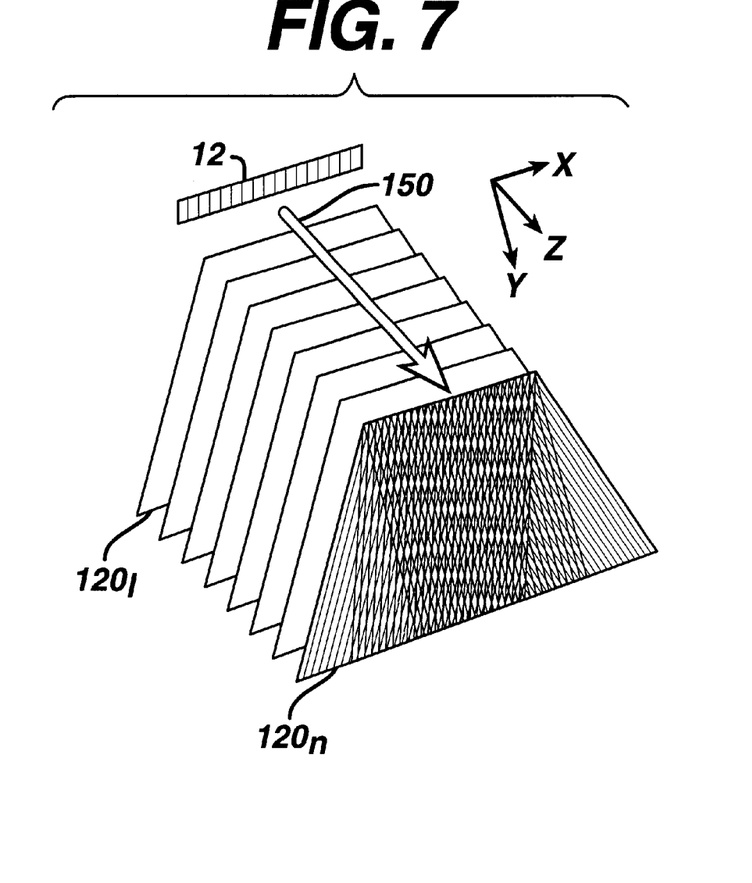
FIG. 7 illustrates the scanning of a volumetric region from different look directions in accordance with the principles of the present invention.
Figure 7A:
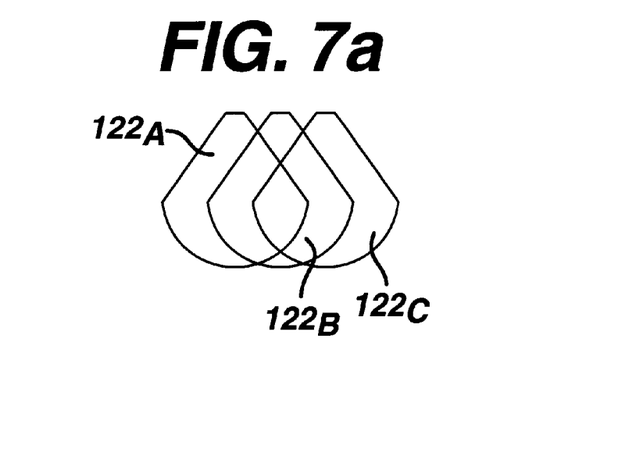

FIG. 7 illustrates one technique for acquiring spatially compounded volumetric image data in accordance with the present invention. A probe including an array transducer 12 is moved above the volumetric region in the z direction as indicated by the arrow 150. The array transducer can be a 1D (single row with only azimuth steering) array, a 1.25D array (multiple rows without electronic focusing in the elevation dimension), a 1.5D array (electronically focused but not steered in the elevation dimension), a 1.75D array (large pitch array with limited three dimensional steering), or a 2D array (fine pitch array with a wide range of three dimensional steering.) As the probe is moved spatially compounded image frames $120_1$–$120_n$ are acquired by scanning component frames A,B,C for compound imaging in rapid succession. FIG. 7 illustrates the use of steered linear component frames in which the scanlines in each component frame are parallel and at differing angles from frame to frame. The component frames could also be offset sector frames $122_A$, $122_B$, $122_C$ each comprising radially steered scanlines as illustrated in FIG. 7a. It will also be appreciated that an increased number of component frames, and hence look directions, will improve the spatially compounded image; a suitable number of component frames for each image can range up to nine or more. By acquiring the component frames for a compound image in rapid succession at successive probe positions the effects of motional blurring are markedly reduced, since there is very little motional effect from one component frame to the next. In addition, there is little need to register the component frames of an individual compound image because the component frames of an image are all referenced to essentially the same probe position. When a single sweep of the probe along arrow 150 is completed, a sequence of spatially compounded image planes of the volumetric region scanned has been acquired which is ready for volume rendering into the desired 3D display format.

The scanning technique of FIG. 7 can be performed freehand if desired. That is, by moving the probe at a relatively steady rate, the image to image spacing in the z (scanning) direction will be relatively uniform, enabling the production of a satisfactory 3D image. Further details of the effectiveness of freehand scanning can be found in Reissued U.S. Pat. No. 36,564. Alternatively, if an anatomically precise 3D image is desired, the component frames can be acquired at accurately spaced increments in the z direction by triggering acquisition from a measure of probe position. This can be done using Doppler methods as explained in U.S. Pat. No. 5,127,409, by a position sensor attached to the probe as explained in U.S. Pat. No. 5,529,070, or by a variety of scanning mechanisms and jigs as are known in the art. By triggering acquisition from a measurement of probe position volumetric data suitable for quantification and measurement can be produced. It will be appreciated that the path 150 of probe travel can be curved or arcuate in either a concave or convex dimension. If the path of travel is concave so that the component frames intersect each other in the volumetric region being scanned, additional spatial compounding will be provided.

Figures 8A, 8B, 9:
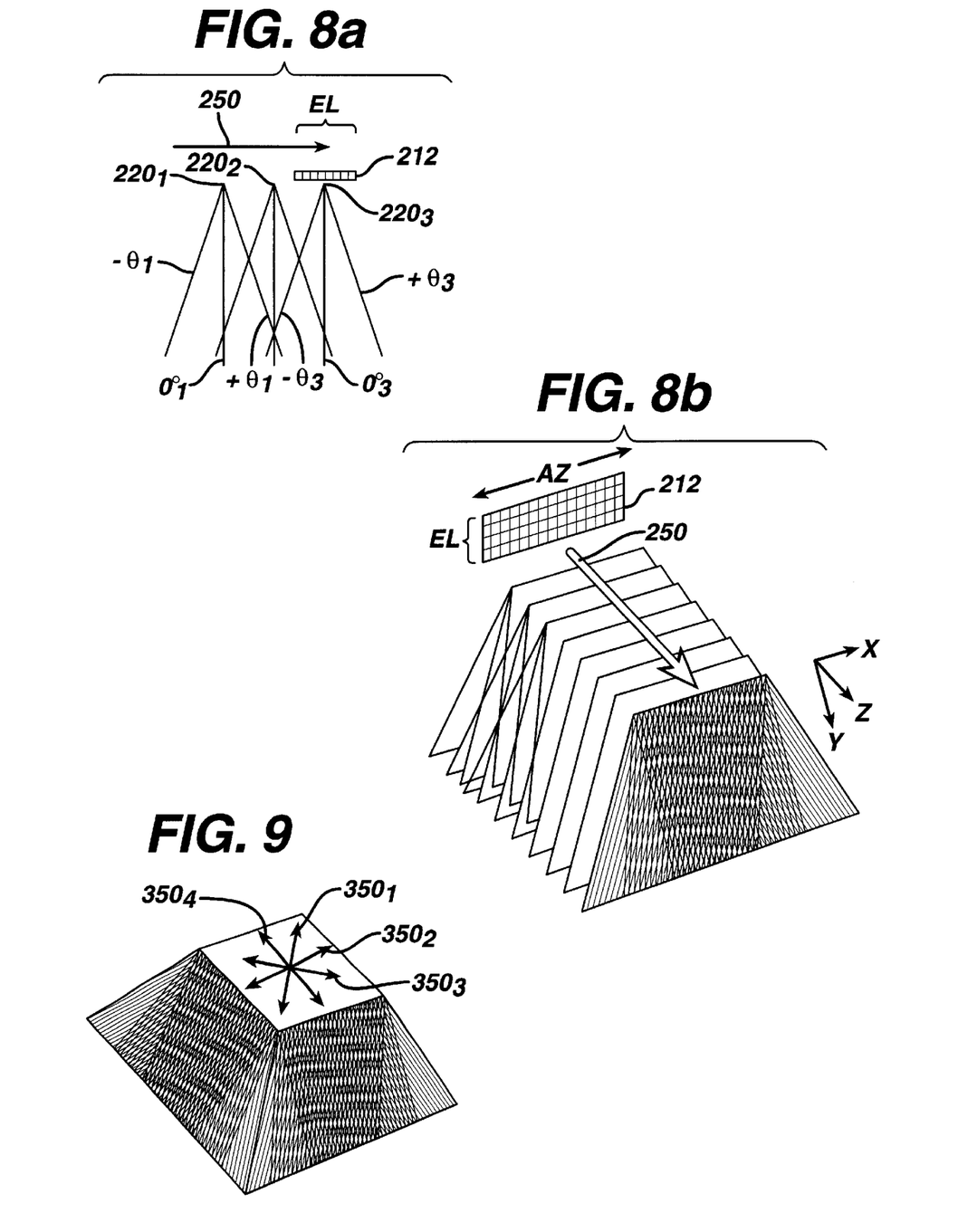
FIGS. 8a and 8b illustrate a technique for acquiring ultrasonic image data from different look directions in multiple intersecting planes during the scanning of a volumetric region.
FIG. 9 illustrates the scanning of a volumetric region by a number of differently directed scanning sweeps.

FIGS. 8a and 8b illustrate another scanning technique in which spatial compounding is performed in two dimensions as the probe is swept over the volumetric region. This technique uses a two dimensional array transducer 212 which is capable of electronically steering beams in both the azimuth (AZ) direction and the elevation (EL) direction. As the probe containing transducer 212 is moved in the z direction as indicated by arrow 250, component frames are acquired for spatial compounding in two or more planar orientations. In the illustrated example, a series of compound images are produced in parallel x-y planes and in planar orientations inclined with respect to the x-y orientation. This is illustrated in FIG. 8a for three different positions $220_1$, $220_2$, and $220_3$ along the scanning path of arrow 250. At position $220_1$ multiple component frames are acquired at angle $0°_1$ which is orthogonal to the plane of the transducer array. These component frames are combined to produce a spatially compounded image in the 0° orientation. By steering the beams in the elevation dimension another set of component frames is acquired in the $-\theta_1$ orientation to produce a second spatially compounded image in the $-\theta$ orientation which is referenced to position $220_1$. The beams are then elevationally steered to the $+\theta_1$ orientation to acquire a third set of component frames for production of a spatially compounded image in the $+\theta$ orientation. Thus, each image plane comprises compounded image information of different look directions, and each of the three image planes is looking in its own unique planar direction within the volume being scanned. This process of acquiring multiple spatially compounded images at different plane orientations is repeated at successive positions as the two dimensional array probe is scanned, as indicated for instance by plane orientations $-\theta_3$, $0_3°$, and $+\theta_3$ for probe location $220_3$. When the scan is completed, three sets of compound images have been acquired over the scanned volume at the three planar orientations. Targets within the volume are thus interrogated by look directions in multiple dimensions for greater volumetric spatial compounding.

It will be appreciated that the technique of FIGS. 8a and 8b may be performed manually in three sweeps by a one dimensional array probe, one with the probe beams oriented straight ahead (0°), another with the probe tipped to the $-\theta$ orientation, and a third with the probe tipped to the $+\theta$ orientation. Since this three sweep scan requires considerably more time than a single sweep, it is preferable for stationary anatomy which is not moving and does not move between sweeps of the probe. Furthermore, three dimensional registration of the sets of data from each sweep will generally be required, either by use of a probe position sensor or by analytical techniques such as image data correlation.

While the transducer scanning paths 150, 250 and 350 in the foregoing examples are shown as straight line paths, it will be appreciated that the paths can be curved in one or more dimensions to scan curving volumetric regions of the body.

FIG. 9 illustrates another scanning technique in which a probe is swept in a plurality of different directions to acquire spatially compounded images. For example, a probe with a linear array 12 may be swept in direction $350_2$ and then direction $350_4$ to acquire two sets of spatially compounded images of a volume in orthogonal planar dimensions. As the other sweep arrows $350_1$, and $350_3$ show, the probe may be swept in additional directions to acquire spatially compounded images in additional planar orientations. Preferably this scanning technique is employed for relatively stationary anatomy and accompanied by three dimensional registration of the image data.

Figure 10:
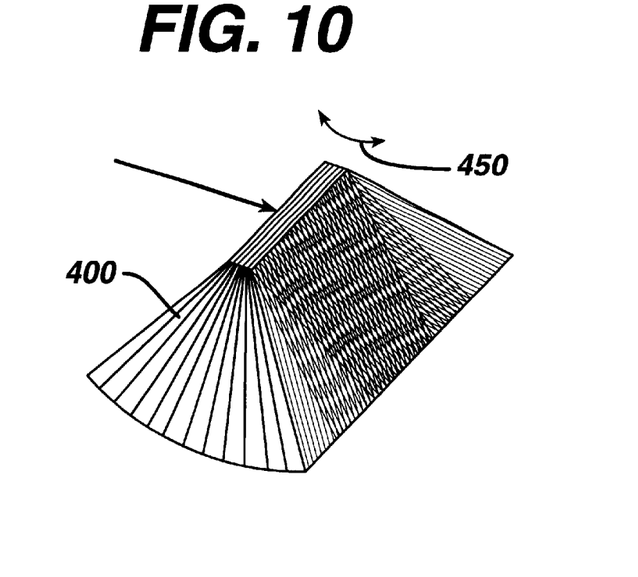
FIG. 10 illustrates the scanning of a volumetric region by the angular sweeping of a transducer image plane.

FIG. 10 illustrates another scanning technique in which a wedge-shaped volume 400 is scanned by moving the probe transducer in an arc. As the probe transducer is rocked in the direction indicated by the arc 450, a series of component images are acquired as the scan plane is fanned through the volumetric region. Since this volumetric spatial compounding scan is performed in a single sweep, it is not constrained to stationary anatomy or registration processing as described for some of the previous techniques. While FIG. 10 illustrates a diverging wedge-shaped volume with the apex of the wedge near the probe transducer, the probe transducer can alternatively be swept in an arc converging at a line remote from the transducer. In this converging scan the individual compound scan planes can be directed to intersect other scan planes, thereby increasing the degree of spatial compounding.

Figure 11:
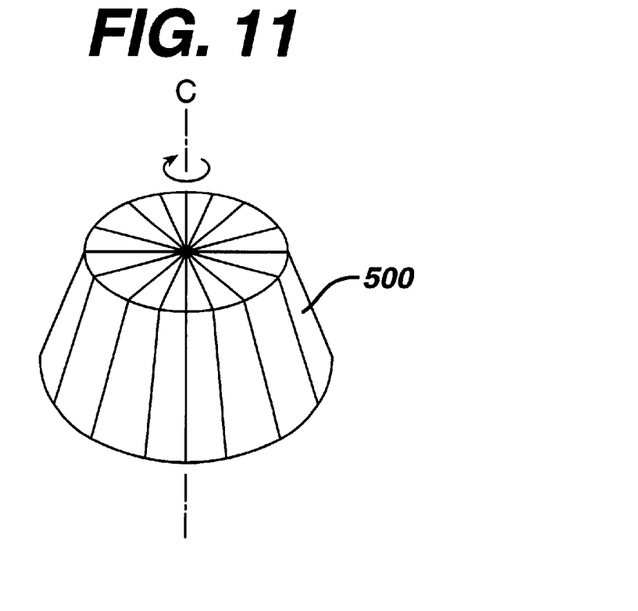
FIG. 11 illustrates the scanning of a volumetric region by the rotation of a transducer image plane.

FIG. 11 illustrates another scanning technique in which the probe transducer is pivoted about a pivot point. Preferably the pivot point is the center C of the transducer array. As the probe is pivoted the image plane sweeps an approximately cylindrical volume 500 with straight or sloping sides. Component images are acquired as the probe is pivoted and compounded to form spatially compounded images at different angular positions around the pivot axis.

What is claimed is:

1. A method of acquiring spatially compounded image data of a volumetric region of the body comprising:
   moving an array transducer along a path to scan a volumetric region of a body;
   acquiring image data from respective targets in the volumetric region at multiple look directions while said transducer traverses said path; and
   processing said image data to form a spatially compounded three dimensional presentation of said volumetric region.

2. The method of claim 1, wherein said step of acquiring comprises acquiring a plurality of image slices, each slice including targets, a plurality of which have been interrogated at multiple look directions.

3. The method of claim 1, wherein said spatially compounded three dimensional presentation comprises a surface rendering.

4. The method of claim 1, wherein said step of processing comprises volume rendering.

5. The method of claim 4, wherein said step of volume rendering produces a kinetic parallax presentation.

6. The method of claim 4, wherein said step of volume rendering produces a maximum intensity projection.

7. The method of claim 4, wherein said step of volume rendering produces an average, mean, or median intensity projection.

8. The method of claim 4, wherein said step of volume rendering further comprises forming a spatially compounded three dimensional presentation of tissue and flow in said volumetric region.

9. The method of claim 8, wherein said step of volume rendering further comprises utilizing variable opacity parameters to form said spatially compounded three dimensional presentation of tissue and flow.

10. The method of claim 1, wherein said step of processing comprises forming one or more images of planes of the volumetric region at one or more planar orientations.

11. The method of claim 1, wherein said step of acquiring comprises acquiring, for each of a plurality of substantially planar target regions in said volumetric region, a plurality of component frames of a common group of targets in said volumetric region which interrogate each of said targets of said common group from a different look direction; and wherein said step of compounding comprises spatially compounding the image data of each of said plurality of component frames.

12. The method of claim 11, wherein each of said plurality of component frames is acquired sequentially in rapid succession.

13. The method of claim 1, wherein said path is located on a surface of said body.

14. The method of claim 1, wherein said path is a straight line.

15. The method of claim 1, wherein said path is an arcuate path about an axis which does not intersect said volumetric region.

16. The method of claim 1, wherein said path is an arcuate path about an axis which intersects said volumetric region.

17. The method of claim 1, wherein said steps of moving and acquiring are repeated for a second path which has a starting point and an ending point and differs from said first named path, wherein said step of processing compounds image data derived from both acquiring steps.

18. The method of claim 1, wherein said step of processing comprises:

compounding said image data to produce spatially compounded image data; and forming a three dimensional presentation of the spatially compounded image data.

19. A method of acquiring spatially compounded image data of a volumetric region of the body comprising:

moving an array transducer along a path from a starting point to an ending point to scan a volumetric region of a body;

acquiring image data when said array transducer is substantially at a first point on said path by two or more beam scanning sequences which scan a portion of said region along different look directions;

acquiring image data when said array transducer is substantially at a second point on said path by two or more beam scanning sequences which scan a portion of said region along different look directions wherein said image data includes data from individual targets in said region which has been acquired by beams steered to said targets from different look directions;

compounding said image data which has been acquired from a common target from different look directions to produce spatially compounded image data; and processing said spatially compounded image data to form a spatially compounded three dimensional presentation of said volumetric region.

20. The method of claim 19, wherein said different look directions extend in different elevation directions.

21. The method of claim 19, wherein said beam scanning sequences comprise substantially planar beam scanning sequences.

22. The method of claim 21, wherein said two or more beam scanning sequences when said transducer is substantially at a given point are of a substantially common slice of said volumetric region.

23. The method of claim 21, wherein said two or more beam scanning sequences when said transducer is substantially at a given point are of substantially parallel slices of said volumetric region.

24. The method of claim 21, wherein said two or more beam scanning sequences when said transducer is substantially at a given point are of non parallel slices of said volumetric region.

25. A method of acquiring spatially compounded image data of a volumetric region of the body comprising:

moving an array transducer along a path from a starting point to an ending point to scan a volumetric region of a body;

acquiring component frames of image data exhibiting spatially different look directions of said volumetric region as said array transducer is moved from said starting point to said ending point; and processing said image data to form a spatially compounded three dimensional presentation of said volumetric region.

26. The method of claim 25, wherein said component frames of said volumetric region are substantially parallel.

27. The method of claim 25, wherein said component frames of said volumetric region are angularly oriented with respect to each other.

28. The method of claim 25, further comprising the step of registering said component frames to reduce the effects of at least one of motion and speed of sound variation.

29. A method of acquiring spatially compounded image data of a volumetric region of the body comprising:

moving an array transducer along a path from a starting point to an ending point to scan a volumetric region of a body;

acquiring spatially compounded image data of said volumetric region as said array transducer is moved from said starting point to said ending point; and processing said spatially compounded image data to form a spatially compounded three dimensional presentation of said volumetric region.

30. The method of claim 29, wherein said spatially compounded image data is acquired in a series of substantially parallel frames of said volumetric region.

31. The method of claim 29, wherein said spatially compounded image data is acquired in a series of relatively angularly oriented frames of said volumetric region.

32. A method of acquiring spatially compounded image data of a volumetric region of the body comprising:

moving an array transducer along a path to scan a volumetric region of a body;

acquiring image data from respective targets in the volumetric region by electronically steering beams in multiple look directions while said transducer traverses said path; and processing said image data to form a spatially compounded three dimensional presentation of said volumetric region.

33. The method of claim 32, further comprising the step of spatially registering said acquired image data.

34. The method of claim 32, wherein said step of processing comprises:

compounding said image data to produce spatially compounded image data; and forming a spatially compounded three dimensional presentation of said volumetric region.

35. A method of acquiring spatially compounded image data of a volumetric region of the body comprising:
- moving an array transducer in a first direction relative to a volumetric region of a body;
- acquiring image data from respective targets in the volumetric region in multiple look directions while said transducer moves in said first direction; and
- processing said image data to form a spatially compounded three dimensional presentation of said volumetric region.

36. The method of claim 35, wherein said multiple look directions comprise second and third directions.

37. The method of claim 36, wherein said image data is acquired in said multiple look directions by electronic beam steering.

38. The method of claim 37, wherein said first direction comprises a substantially straight path.

39. The method of claim 37, wherein said first direction comprises a path which is not a straight path.

40. An ultrasonic diagnostic imaging system which produces spatially compounded images of a volumetric region of the body comprising:
- a movable array transducer which can be moved along a path to scan a volumetric region of the body and acquire ultrasonic image data;
- a beam steering circuit, coupled to said array transducer, which steers beams in multiple intersecting look directions during scanning of said volumetric region;
- a compound image processor, responsive to said acquired ultrasonic image data, which compounds said image data on a spatial basis; and
- an image display, responsive to said compound image processor, which displays a spatially compounded image of said volumetric region.

41. The ultrasonic diagnostic imaging system of claim 40, wherein said beam steering circuit acts to electronically steer beams in multiple look directions while said transducer traverses said path.

* * * * *